US005434065A

United States Patent [19]

Mahan et al.

[11] Patent Number: 5,434,065
[45] Date of Patent: Jul. 18, 1995

[54] IN VIVO SELECTION OF MICROBIAL VIRULENCE GENES

[75] Inventors: Michael J. Mahan, West Roxbury; John J. Mekalanos, Cambridge; James M. Slauch, Natick, all of Mass.

[73] Assignee: President and Fellows of Harvard College, Cambridge, Mass.

[21] Appl. No.: 58,299

[22] Filed: May 6, 1993

[51] Int. Cl.⁶ .................... C12N 15/09; C12N 15/10
[52] U.S. Cl. ......................... 435/172.3; 435/91.1; 435/91.41; 435/243; 435/252.3; 935/79
[58] Field of Search ............... 435/172.3, 172.1, 29, 435/34, 317.1, 91.1, 91.4, 91.41, 252.3, 243; 935/179, 111

[56] References Cited

PUBLICATIONS

Mahan, M. J. et al. 1993. *Science* vol. 259 pp. 686–688.
Barinaga, M. 1993. Science vol. 259 p. 595.
"Environmental Signals Controlling Expression of Virulence Determinants in Bacteria," by J. Mekalanos, J. Bacteriology 174, 1 (1992).
"Mutants of *Salmonella typhimurium* that Cannot Survive With the Macrophage are Avirulent," by P. Fields, et al. Pro. Natl. Acad. Sci. USA 83, 5189–5193 (1986).
"A Single Genetic Locus Encoded by *Yersinia pseudotuberculosis* Permits Invasion of Cultured Animal Cells by *Escherichia coli* K–12," by R. Isberg, et al., Nature, 317, 262–264 (1985).
"Identification of Plunt Induced Genes of the Bacterial Pathogen *Xanthomonas campestris* Pathovar compestris using a Promoter–Probe Plasmid," by A. E. Osborn, et al. EMBO J., 6, 23–28 (1987).
"Two trans-acting Regulatory Genes (*vir and mod*) Control Antigenic Modulation in *Bordetella pertussis*", by S. Knapp, et al., J. Bacteriol 170, 5059–5066 (1988).
"A Novel Suicide Vector and its use in Construction of Insertion Mutation: Osmoregulation of Outer Membrane Proteins and Virulence Determinants in *Vibrio cholera* Requires toxR," by V. Miller, et al. J. Bacteriol 170, 2575–2583 (1988).

*Primary Examiner*—Mary E. Mosher
*Attorney, Agent, or Firm*—Steven C. Petersen; Chrisman, Bynum & Johnson

[57] ABSTRACT

A genetic system termed in vivo expression technology was devised that positively selects for microbial genes that are specifically induced when microbes infect their host. The method of this invention comprises complementing the growth of an auxotrophic or antibiotic sensitive microorganism by integrating an expression vector by way of homologous recombination into the auxotrophic or antibiotic sensitive microorganism's chromosome and inducing the expression of a synthetic operon which encodes transcripts, the expression of which are easily monitored both in vitro and in vivo.

21 Claims, 7 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (other)

( i i i ) HYPOTHETICAL: NO ( i v ) ANTI-SENSE: NO ( x i ) SEQUENCE DESCRIPTION: SEQ ID NO:1:

GAATCCAGTC GACAGCAAAC GGTG  24

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (other)

( i i i ) HYPOTHETICAL: NO ( i v ) ANTI-SENSE: YES ( x i ) SEQUENCE DESCRIPTION: SEQ ID NO:2:

CAGGGGTACC AGAATTACGC GTC  23

( 2 ) INFORMATION FOR SEQ ID NO:3:

( i ) SEQUENCE CHARACTERISTICS:

(A) LENGTH: 25 base pairs
(B) TYPE: nucleic acid
(C) STRANDEDNESS: single
(D) TOPOLOGY: linear (ii) MOLECULE TYPE: DNA (other)

(iii) HYPOTHETICAL: NO (iv) ANTI-SENSE: NO (xi) SEQUENCE DESCRIPTION: SEQ ID NO:3:

AGCAACAGGT ACCTGAGGAA CCATG    25

(2) INFORMATION FOR SEQ ID NO:4:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (other)

(iii) HYPOTHETICAL: NO (iv) ANTI-SENSE: YES (xi) SEQUENCE DESCRIPTION: SEQ ID NO:4:

TGGCAGGATG AATTCTTAGA TAGCCACC    28

IN VIVO SELECTION OF MICROBIAL VIRULENCE GENES

CONTRACTUAL ORIGIN OF THE INVENTION

This study was supported by National Institutes of Health grant AI26289 (to J. J. M.), National Research Service Award AI08245 (to M. J. M.), and Damon Runyon-Walter Winchell Cancer Research Fund DRG-1061 (to J. M. S.), and has been assigned to the President and Fellows of Harvard College.

BACKGROUND OF THE INVENTION

1. Field of the Invention

The present invention relates to in vivo expression technology, and more particularly to a method for selecting microbial virulence genes that are specifically induced in host tissues.

2. Description of the State of the Art

An infection of the human body by a pathogen, or disease-producing microorganism, results in disease when the potential of the microorganism to disrupt normal bodily functions is fully expressed. Some disease-producing microorganisms possess properties, referred to as virulence factors, that enhance their pathogenicity and allow them to invade host or human tissues and disrupt normal bodily functions. The virulence of pathogens, that is, their ability to induce human disease, depends in large part on two properties of the pathogen, invasiveness and toxigenicity. Invasiveness refers to the ability of the pathogen to invade host or human tissues, attach to cells, and multiply within the cell or tissues of the human body. Toxigenicity refers to the ability of a pathogen to produce biochemicals, known as toxins, that disrupt the normal functions of cells or are generally destructive to cells and tissues.

Scientists can develop better therapeutic and diagnostic approaches against pathogenic microbes if they understand better the molecular mechanisms of the specific pathogenic microbes or microorganisms that allow them to circumvent the host's, e.g., human body, immune system and initiate the physiological changes inherent in the disease process. To do so, scientists must identify those virulence factors, or microbial gene products, that are specifically required for each stage of the infection process. Environmental conditions within the host are responsible for regulating the expression of most known virulence factors, (J. Mekalanos, *J. Bacteriol.* 174, 1 (1992)). Consequently, scientists attempt to mimic, in vitro, the environmental conditions within the host in an attempt to identify those genes that encode and are responsible for producing virulence factors. As a result, the identification of many virulence factors has been dependent on, and limited by, the ability of researchers to mimic host environmental factors in the laboratory.

There have been some methods developed for identifying virulence genes of microorganisms involved in pathogenesis. For example, a method referred to as insertional mutagenesis has long been recognized as a technique to inactivate and identify genes. Insertional mutagenesis relies on the ability of short stretches of DNA, known as insertion sequences, to move from one location to another on a chromosome by way of nonreciprocal recombination. Insertion sequences are not homologous with the regions of the plasmid or the chromosome into which the insert. Therefore, independent mutational events may be generated by randomly inserting an insertion sequence into a gene, thereby, disrupting the expression of that gene. As each mutated gene represents a different case, the selection procedure utilized in successfully recovering insertional mutants is critical. In vitro assays are designed to screen for insertional activation events, i.e., the turning "on" of a previously silent gene, or insertional inactivation events, i.e., the turning "off" of a previously expressed gene. For an example of the insertional mutagenesis method see Fields et al., *Proc. Natl. Acad. Sci. USA* 83, 5189–5193, 1986.

The second basic technique utilized in the screen. Essentially, a piece of DNA or gene from the organism of interest is spliced into either a plasmid or a lambda phage, referred to as the vehicle or vector, and the resulting chimeric molecule is used to transform or infect, respectively, a host cell. A determination is then made as to whether the piece of DNA or gene of interest is capable of conferring a specific phenotype to the host cell which it would not otherwise possess, but for the gene of interest. For example, R. Isberg et al., in a technical paper entitled "A Single Genetic Locus Encoded by *Yersinia pseudotuberculosis* Permits Invasion of Cultured Animal Cells by *Escherichia* coli K-12," *Nature*, 317, 262–264, 1985, discloses a cloning screen in which a cosmid clone bank similar to that of a lambda phage, is prepared from *Y. pseudotuberculosis* and introduced into a bacterial *E. coli* K-12 strain. The *E. coli* K-12 strain containing random sequences of DNA representing the entire genetic information for *Y. pseudotuberculosis* was pooled, grown in broth, i.e., a complete medium, and used to infect a monolayer of cultured HEp-2 cells, i.e., animal cells. The cultured animal cells were then cultured and tested to determine whether introducing DNA from *Y. pseudotuberculosis* to *E. coli* confers an invasive phenotype typical of *Y. pseudotuberculosis* to *E. coli*.

A third method discussed by A. Osbourn et al., entitled "Identification of plant induced genes of the bacterial pathogen *Xanthomonas campestris* pathovar *campestris* using a promoter-probe plasmid", EMBO J., 6, 23–28, 1987, discloses a promoter probe plasmid for use in identifying promoters that are induced in vivo. Random chromosomal DNA fragments are cloned into a site in front of a promoterless chloramphenicol acetyltransferase gene contained in a plasmid. Transconjugates were then produced by transferring the resulting library into Xanthomonas. Individual transconjugates are then introduced into chloramphenicol-treated seedlings to determine whether the transconjugate displays resistance to chloramphenicol in the plant and then on an agar plate.

The final method utilized in the identification of genes is referred to as a regulatory screen. S. Knapp et al., in his technical publication, entitled "Two Trans-Acting Regulatory Genes (vir and mod) Control Antigenic Modulation in *Bordetella pertussis*," *J. Bacteriol* 170, 5059–5066, 1988, discloses a method for identifying potential virulence genes based on their coordinate expression with other known virulence genes under defined laboratory conditions.

The above technical papers by Fields et al., R. Isbert et al., and S. Knapp et al., each disclose methods for identifying microorganismal genes; however, the selection procedures or in vitro assays utilized in each method depends upon the ability of the in vitro assay to mimic the environmental conditions within the host, i.e., the in vivo environmental conditions. A disadvantage of these approaches is that each requires some understanding of the environmental conditions necessary to obtain virulence expression. Consequently, scientists have resorted to mixing host cells with the pathogen of interest in vitro to approximate the host's environmental conditions. Short of an exact duplication of the host's environmental conditions, critical regulatory factors necessary for the expression of many virulence factors may be missing, thus making the identification of those genes responsible for encoding virulence factors impossible to identify.

While the technical paper by A. Osbourn, et al., discloses a method to screen for promoters that are induced in vivo, a disadvantage is that no feasible method exists to select genes of a particular class, that is, individual transconjugates must be screened one by one in individual seedlings to determine whether a promoter is inducible. A further disadvantage results from a phenomena referred to as a position effect. A. Osbourn et al., utilize an autonomous plasmid and therefore the regulation of the promoter may vary considerably from the regulation of the promoter as it is found in its natural environment on the Xanthomonas genome. Other complications that arise from the use of plasmids are copy number, stability and super coiling effects.

There is still a need, therefore, for a method or technique for identifying genes encoding virulence factors in their normal environment whose expression is regulated, or turned "on", by undetermined factors within the host.

SUMMARY OF THE INVENTION

Accordingly, it is an object of this invention to provide a method for the identification of microbial genes that are specifically induced within the host tissues.

Additional objects, advantages and novel features of this invention shall be set forth in part in the description that follows, and in pan will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method of this invention comprises complementing the growth of an auxotrophic or antibiotic sensitive microorganism by integrating an expression vector by way of homologous recombination into the auxotrophic or antibiotic sensitive microorganism's chromosome and inducing the expression of a synthetic operon which encodes transcripts, the expression of which are easily monitored both in vitro and in vivo.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

In the Drawings.

DETAILED DESCRIPTION OF THE PREFERRED EMBODIMENT

Figure 1:
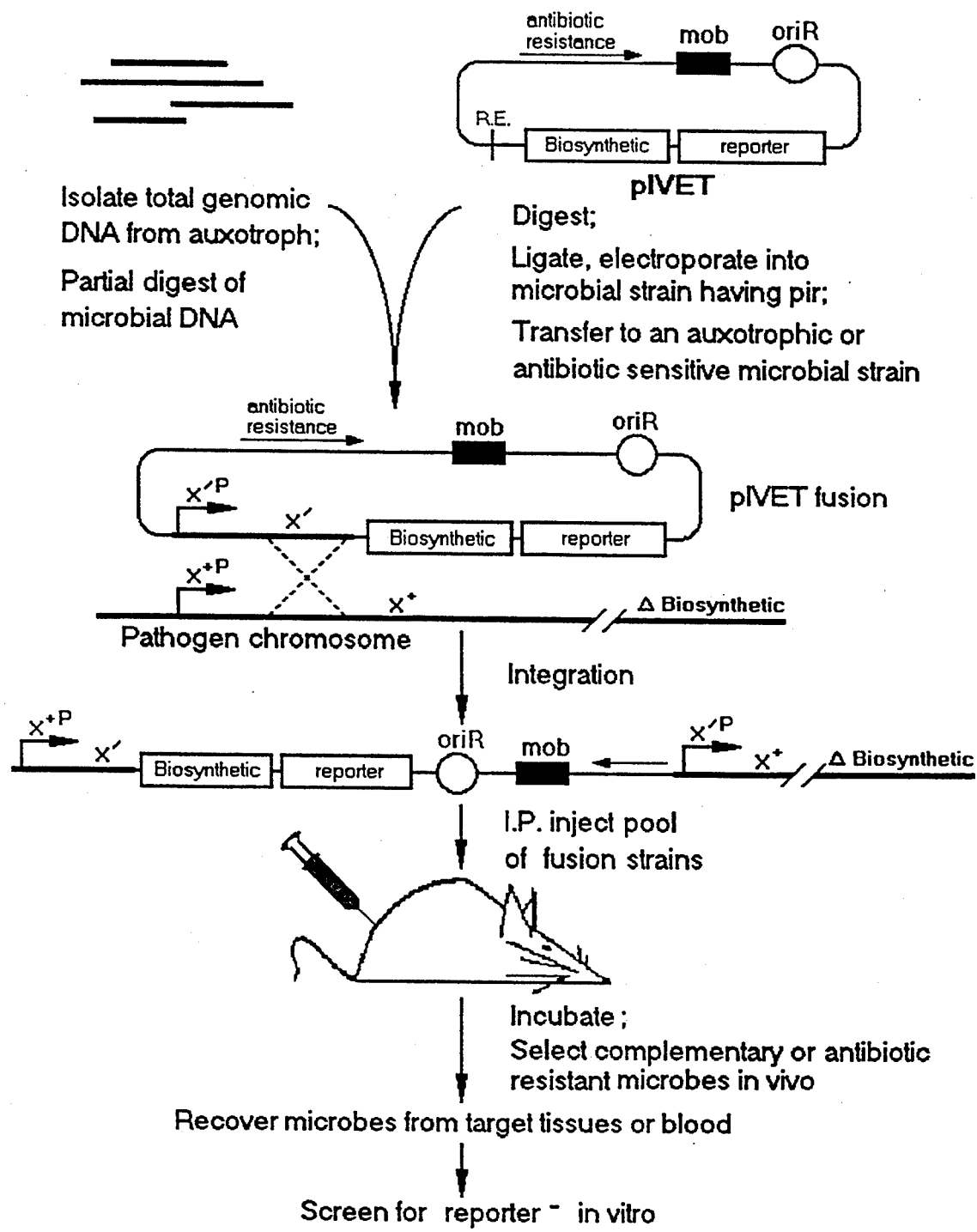
FIG. 1 is a flow sheet representing the method of positive selection for in vivo induced (ivi) genes that are specifically induced in the host.
Figure 2:
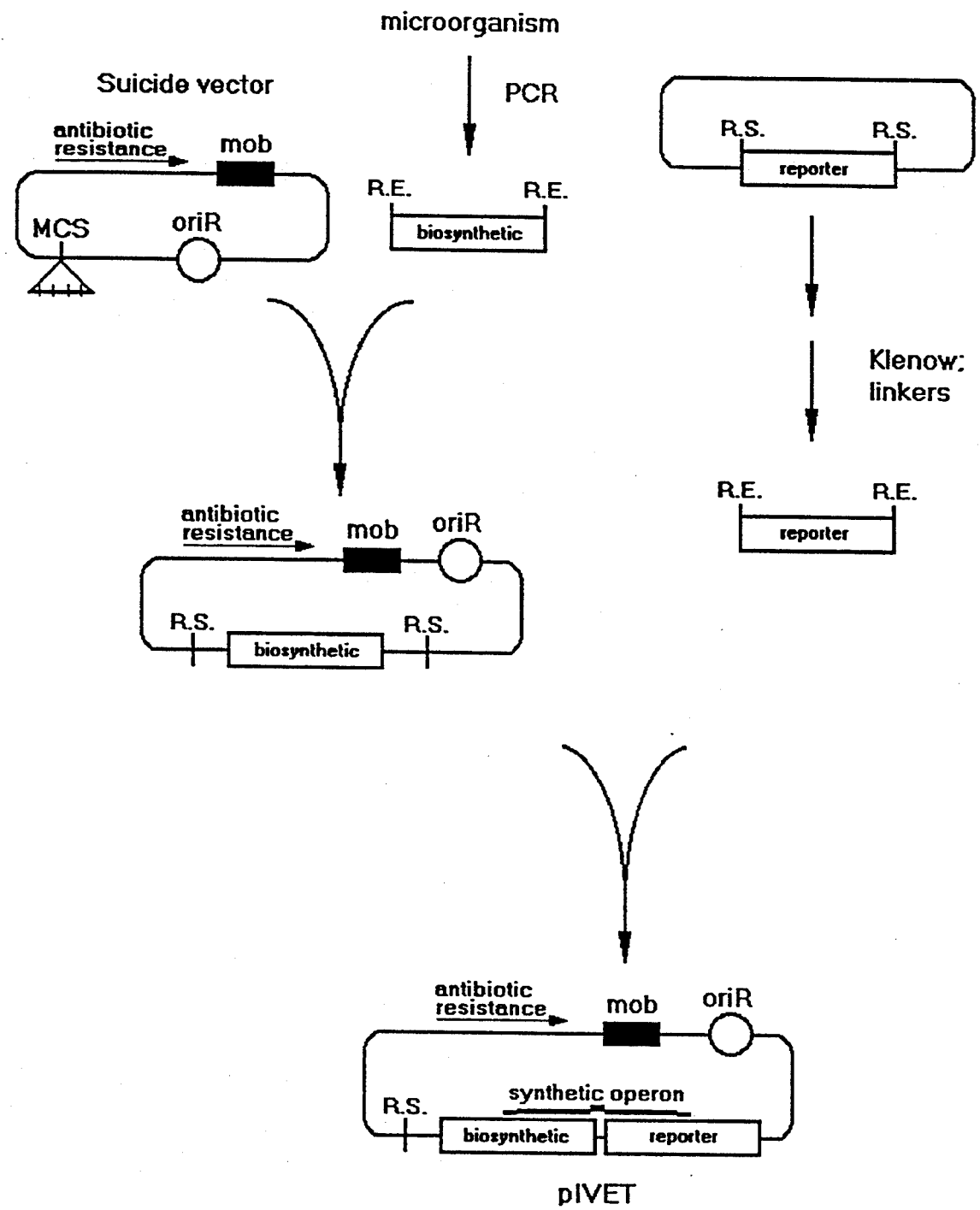
FIG. 2 is a diagrammatic representation of the construction of the pIVET vector.

The genetic method or system termed in vivo expression technology (IVET), according to this invention, as shown in FIG. 1, does not rely on the reproduction of the host's environmental signals in the laboratory, but rather depends directly upon the induction or activation of micobial genes within the host itself. Plasmid or vector pIVET, constructed as shown in FIG. 2, provides several significant functions for purposes of this invention. First, vector pIVET provides a method for introducing and integrating a single copy of foreign genetic material or DNA into the recipient organism's s genome, thereby avoiding any complications such as copy number, stability or supercoiling effects that may arise from the use of plasmids that replicate autonomously within the cell. Second, the integration event does not disrupt any chromosomal genes of the recipient microorganism. If a gene of interest encodes a product required for the infection process, i.e., a virulence factor, then any integration event which disrupts the gene would not be recoverable. Third, the transcriptional activity of the integrated foreign DNA can be monitored both in vitro and in vivo.

Plasmid pIVET comprises a suicide vector for receiving and introducing foreign genetic material into a recipient cell, a synthetic operon for expressing gene products which are easily monitored both in vitro and in vivo, and a restriction or cloning site (shown as R.S. in FIG. 2) for cloning a random homologous fragment of chromosomal DNA. The pIVET vector having a cloned fragment of DNA is referred to as a pIVET fusion.

Suicide vectors are essentially shuttle vectors that provide a means for introducing foreign genetic material into a recipient cell. However, unlike a typical shuttle vector, suicide vectors have replicons that are not independently maintainable within the recipient cells, i.e., as the cells propagate, the suicide vector, being incapable of autonomous replication, will be lost in subsequent cells. Consequently, integration of the pIVET fusion into the recipient cell's genome is required for the continued survival of the pIVET fusion within the recipient cell. One of the genes present on the suicide vector encodes for antibiotic resistance, such as the β-lactamase or bla gene, which confers resistance to the antibiotic ampicillin. Therefore, a simple and convenient method of monitoring whether integration of the pIVET fusion, into the recipient's genome, has occurred is to expose the recipient cells to an antibiotic for which they are typically's sensitive and to select those cells which are resistant. Cells that display resistance to the antibiotic are those which have the pIVET fusion integrated into and replicated with the recipient cell's genome. Those cells in which the pIVET fusion was not integrated into the genome eventually lose the pIVET fusion and remain sensitive to the antibiotic.

Essentially, the genetic system of the present invention originates with an auxotroph or a deficient microorganism that is carrying a mutation or a deletion of a biosynthetic pathway gene encoding a functional biosynthetic enzyme necessary for that microorganisms growth in vivo, thus the auxotroph's growth is greatly attenuated in vivo. Biosynthetic pathways are well known and extensively studied. An example of a biosynthetic pathway is one that converts a carbon source into a useable energy source. This is done by a series of enzyme catalyzed reactions. Each enzyme is encoded by a different gene. Many biosynthetic pathways are common among organisms with each organism having a closely related homologous set of enzymes serving homologous functions in the series of reactions. When a functional or wild type copy of a biosynthetic pathway gene is inserted into an auxotroph, the expression of that wild type biosynthetic pathway gene provides the auxotroph with the necessary biosynthetic enzyme required for survival. The homologous biosynthetic enzyme performs the catalytic function in the biosynthetic pathway and thereby confers to the auxotroph the ability to survive and propagate. The process of replacing a missing or non-functional gene of an auxotroph with a functional homologous gene in order to restore the auxotroph's ability to survive within a host is called "complementation."

Complementation of the auxotroph, according to the present invention is accomplished through the construction and expression of a synthetic operon. As shown in FIG. 2, the synthetic operon is comprised of two promoterless genes that have been isolated and fused together directionally oriented downstream of the pIVET cloning or restriction site. Orientation refers to the directionality of the structural gene. That portion of a structural gene which ultimately codes for the amino terminus of the protein is termed the 5'-end of the structural gene, while that end which codes for the amino acid near the carboxyl end of the protein is termed the 3'-end of the structural gene. Correct orientation of the structural gene is with the 5'-end thereof proximal to the promoter. A promoter contains specific base-pair sequences which lie at the 5'-end of a gene and are responsible for binding an enzyme, RNA polymerase, which initiates transcription of a gene. These base-pair sequences are not gene specific; therefore, a promoter region operatively linked to any gene or set of genes will control the expression of that gene or that set of genes, respectively, dependent on the proper regulatory factors or enzyme modifications being present to allow RNA polymerase to recognize the specific transcription sites. The region of DNA lying under promoter control is said to lie "downstream" or alternatively "behind" or "3'to" the promoter. Therefore, to be controlled by the promoter the correct position of the gene must be downstream from the promoter. However, the synthetic operon as constructed lacks the specific base pair sequences necessary for the initiation of transcription. Therefore, the products encoded for by the synthetic operon are incapable of being expressed unless a promoter sequence exists in the region of the recipient's chromosome that is homologous to the fragment of DNA which is inserted into the cloning site of the pIVET vector situated 5' to the synthetic operon.

The first gene of the synthetic operon, i.e., the gene lying immediately downstream from the cloning site, encodes a biosynthetic pathway enzyme of a microorganism which relies on such an enzyme for survival. This biosynthetic pathway gene if activated will complement the growth of the auxotroph, deficient for the same biosynthetic pathway gene, into which it is inserted. As discussed previously, many biosynthetic pathways are common among organisms with each organism having a closely related homologous set of enzymes serving homologous functions in a series of catalyzed reactions essential for survival. The biosynthetic pathway gene of the synthetic operon is isolated from a microorganism other than the auxotroph to be complemented. The enzyme produced by this biosynthetic pathway gene serves a homologous function of the deficient enzyme and is capable of complementing the growth of the auxotrophic microorganism; however, the gene sequence itself is divergent from the sequence of the mutated biosynthetic pathway gene of the auxotroph so that recombination will not occur between the mutated biosynthetic pathway gene of the auxotroph and the wild type biosynthetic pathway gene of the synthetic operon.

The second gene of the synthetic operon is a reporter gene that lies immediately downstream from the biosynthetic pathway gene and encodes a reporter enzyme. Expression of the reporter gene can be easily detected by colorimetric assays which are well known and understood in the art. Furthermore, the auxotroph does not contain a gene homologous to the reporter gene. Consequently, the only site in the pIVET vector capable of homologous recombination with the recipient's chromosome is that fragment of DNA which is cloned into the restriction site 5' to the synthetic operon.

Referring now to FIG. 1, total genomic DNA is isolated from the auxotrophic strain and then partially enzymatically digested, resulting in a pool of random chromosomal fragments. The pIVET vectors, which have previously been cleaved at the restriction or cloning site, are then mixed into this pool of random chromosomal fragments. The chromosomal fragments are ligated into the pIVET vectors to produce a library of pIVET fusions, i.e., each pIVET fusion contains a random chromosomal fragment so that the pool of pIVET fusions is representative of the entire auxotrophic genome. The pIVET fusions are then electroporated into a microorganism that supplies the replication protein, II, which is required for replication by the suicide vector, as will be discussed in further detail below. The pIVET fusions are then introduced or injected into the auxotrophic microorganism, by well known methods, for example, transduction, transformation, electroporation, tri-parental mating technique or direct transfer of a self-mobilized vector in a bi-parental mating.

After the pIVET fusion is introduced into the auxotrophic microorganism, a couple of possible events may occur. For example, complete degradation of the pIVET fusion may occur due to the restriction modification system that many microorganisms possess, or there could be integration of the pIVET fusion into the auxotroph's genome by homologous recombination. The former event is highly probable in that many microorganisms contain systems to guard against the invasion of foreign DNA. The cells contain specific endonucleases that make double strand scissions in invading DNA, thus degrading the pIVET fusion. The latter event of integration through a process referred to as homologous recombination is an essential step to the method of the present invention, and this event can be selected by the use of antibiotics as described previously. As discussed above the only DNA sequences of the pIVET fusion that share sufficient homology with the chromosome of the recipient strain to allow the recombination event are those random chromosomal fragments which were inserted 5' to the synthetic operon. Consequently, only these random fragments share sufficient homology with the recipient's genome, and it is through these homologous sequences of DNA that the integration event of the pIVET fusion and the recipient cell's genome takes place, thus resulting in a fusion strain.

Figure 3:
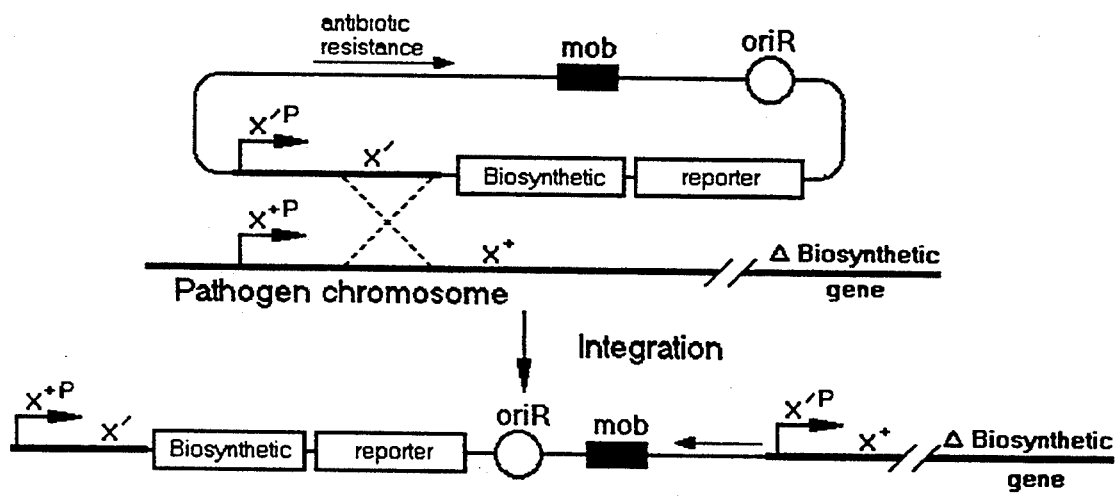
FIG. 3 is a diagrammatic representation of the homologous recombination event which occurs between the pIVET fusion and the pathogen chromosome.
Figure 4:
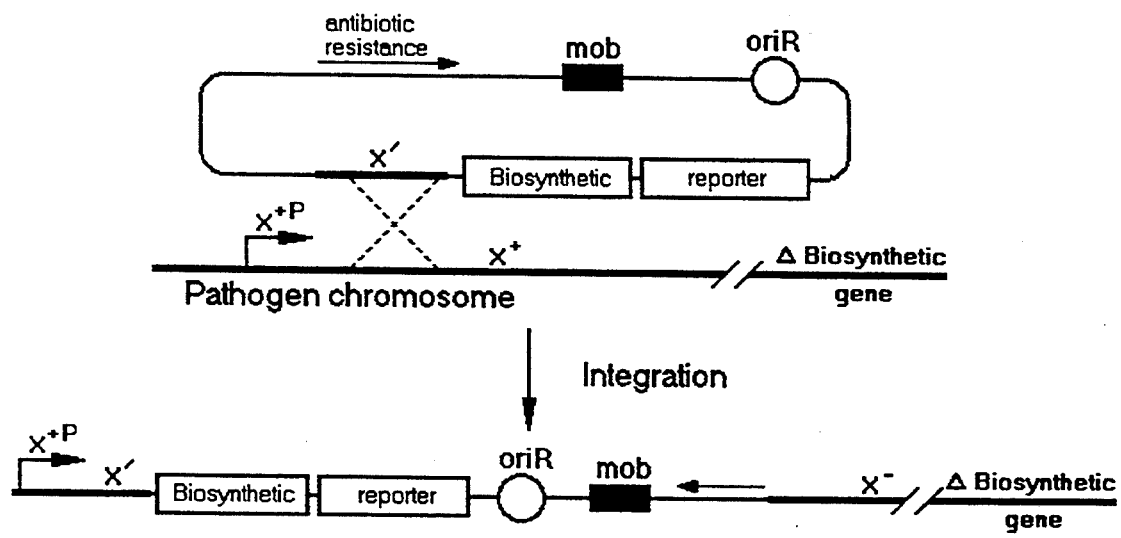
FIG. 4 is a diagrammatic representation of the manner in which the expression of a wild type gene on the pathogen chromosome may be disrupted as a result of the homologous recombination event with the pIVET fusion which lacks a cloned promoter region.

The desired integration event is illustrated in FIG. 3. The cloned chromosomal fragment $X'$ containing a promoter sequence $X'^p$ is homologous to and recombines with its respective or wild type sequence $X^+$ located in the auxotroph's chromosome. The promoter of the wild type gene designated $X^{+p}$ is now operatively linked to and controls the expression of the synthetic operon, whereas the wild type gene, $X^+$, of the auxotroph is now linked to and under the control of the $X'^p$ promoter. The importance of this event is that the integration event does not disrupt any chromosomal genes that may be necessary for the infection process. The manner in which an integration event could lead to the disruption of a chromosomal gene is illustrated in FIG. 4. The chromosomal fragment $X'$ inserted into the pIVET vector may not have a promoter sequence, or the promoter sequence may be in the wrong orientation with respect to the gene (not shown) which it is to control. In either event, homologous recombination will occur between the cloned chromosomal fragment, $X'$, and the auxotroph's chromosome, $X^+$. However the promoter of the wild type gene, $X^{+p}$, will initiate transcription of the synthetic operon, while the wild type gene will not be expressed, since it will now lack a promoter. If the wild type gene, X, that is disrupted through this integration event is essential to the infection process it will not be recoverable as those microorganisms will not be infectious and will not survive within the host.

As shown in FIG. 1, the pool of integrated fusion strains is injected intraperitoneally into a host. After a period of infection, the host is sacrificed and the organs, tissues, or blood which are the targets of infection for the pathogenic microorganism used to infect the host are removed and homogenized. Survival of the microorganisms within the host is an indication that the biosynthetic pathway gene necessary for growth was being expressed and that a chromosomal gene required for the infection process was not disrupted. The surviving microorganisms are harvested and then cultured and plated out on a medium, which produces a color change in response to the expression of the reporter gene. Most of the colonies that grow on the plate produce a color change which indicates that the expression of the reporter gene of the synthetic operon was induced or turned "on" in vitro. These genes that are "on" on laboratory medium are also "on" in the host due to a constituitively induced promoter. Colonies that remain colorless indicate that the reporter gene is not capable of being expressed or "off" in vitro. These colonies, those that are "off" in vitro, contain fusions to the genes of interest. These genes are "on" in the host, but are "off" on laboratory medium.

To confirm that these fusions are specifically induced in vivo, the reporter enzyme activity of microorganisms recovered from the organs, blood, or tissues of the infected host may be assayed directly, and the activity compared to that measured for the same strain grown over night in rich medium.

In another embodiment of the present invention (not shown), a synthetic operon may be constructed, which is comprised of a gene encoding for antibiotic resistance fused to a reporter gene. The pIVET vector having this synthetic operon is then inserted into a microorganism that is sensitive to the antibiotic for which the first gene of the synthetic operon confers resistance. The host to be infected is treated with an antibiotic and then challenged with the pool of fusion strains. Successful selection is monitored, as described above, by harvesting the surviving fusion strains, plating the selected pool of fusion strains, and noting color changes in response to production of the reporter enzyme. Antibiotic selection will be of general use, particularly in systems where it is difficult to obtain auxotrophic mutations or in tissue cultures systems where depletion of nutrients is less feasible.

In a third embodiment (not shown), the fusion strains that confer antibiotic resistance are incubated in a tissue culture, thus infecting the cells of the tissue culture. An antibiotic is then introduced to the tissue culture effectively killing all fusion strains that have not invaded the cells. The antibiotic used is incapable of penetrating the mammalian cells, thus, the fusion strains which have invaded the mammalian cells survive. The mammalian cells are then incubated with a different antibiotic, which is capable of penetrating the mammalian cells. Thus, the fusion strains that survive this assay are those which are resistant to the antibiotic due to the, expression of the synthetic operon. The fusion strains are then isolated from the mammalian cells and plated out on an indicator medium as discussed above. As discussed previously, those fusion strains which survive within the mammalian cells are those which have promoters that have been induced and are controlling the expression of the synthetic operon which confers resistance to the antibiotic. The colonies appearing on the indicator medium that do not produce a color change are indicative of promoters that are not induced in vitro. The importance of this embodiment is that it is a selection process whereby genes which are induced in specific tissues, e.g. tissue culture macrophages may be isolated.

All of the IVET systems to date contain a promoterless lac operon as the reporter system to allow convenient monitoring of transcriptional activity in vitro and in vivo. The lac system has many advantages, including a variety of substances for use in assays and selections (J. Slauch et at., *Methods Enzymol.* 204, 213 (1991) and J. H. Miller, A short course in bacterial genetics a laboratory manual and handbook for *Escherichia coli* and related bacteria (Cold Spring Harbor Laboratory Press, Plainview, N.Y., 1992)). The main advantage is the ability to select lacZ expression (Lac+) on plates. However, this capability may not be feasible in all organisms. Indeed, in some organisms it may be necessary to use a reporter system other than lacZ. For example, a promising new reporter gene encoding firefly luciferase has recently been characterized (J. de Wet et al., *Molec. Cell Biol.* 7, 725 (1987)), and the human growth hormone (hGH) gene offers several advantages as a reporter function (R. Seldon et al., *Mol. Cell. Biol.* 6, 3173 (1986)). Of course regardless of whichever reporter system is ultimately used, the method of this invention will require a method of monitoring transcriptional activity in order to determine whether the reporter system was induced or activated, thereby indicating which microorganisms can be selected for purposes of this invention. The genetic method of the present invention was designed to facilitate the identification of genes which encode for virulence factors, not only in bacteria, but also in other, pathogenic microorganisms, including viruses, parasites, fungi and protozoa thereby contributing to vaccine and antimicrobial drug development. For example, in vivo induced genes may encode new antigens, and mutations in in vivo induced genes may provide an additional means of constructing live attenuated vaccines. Multivalent vaccines in which a single live vaccine is engineered to make several. antigens, immunizing against several diseases at once could also be designed with the identification of new virulence genes.

EXAMPLE 1

Construction of the pIVET1 Vector

Figure 5:
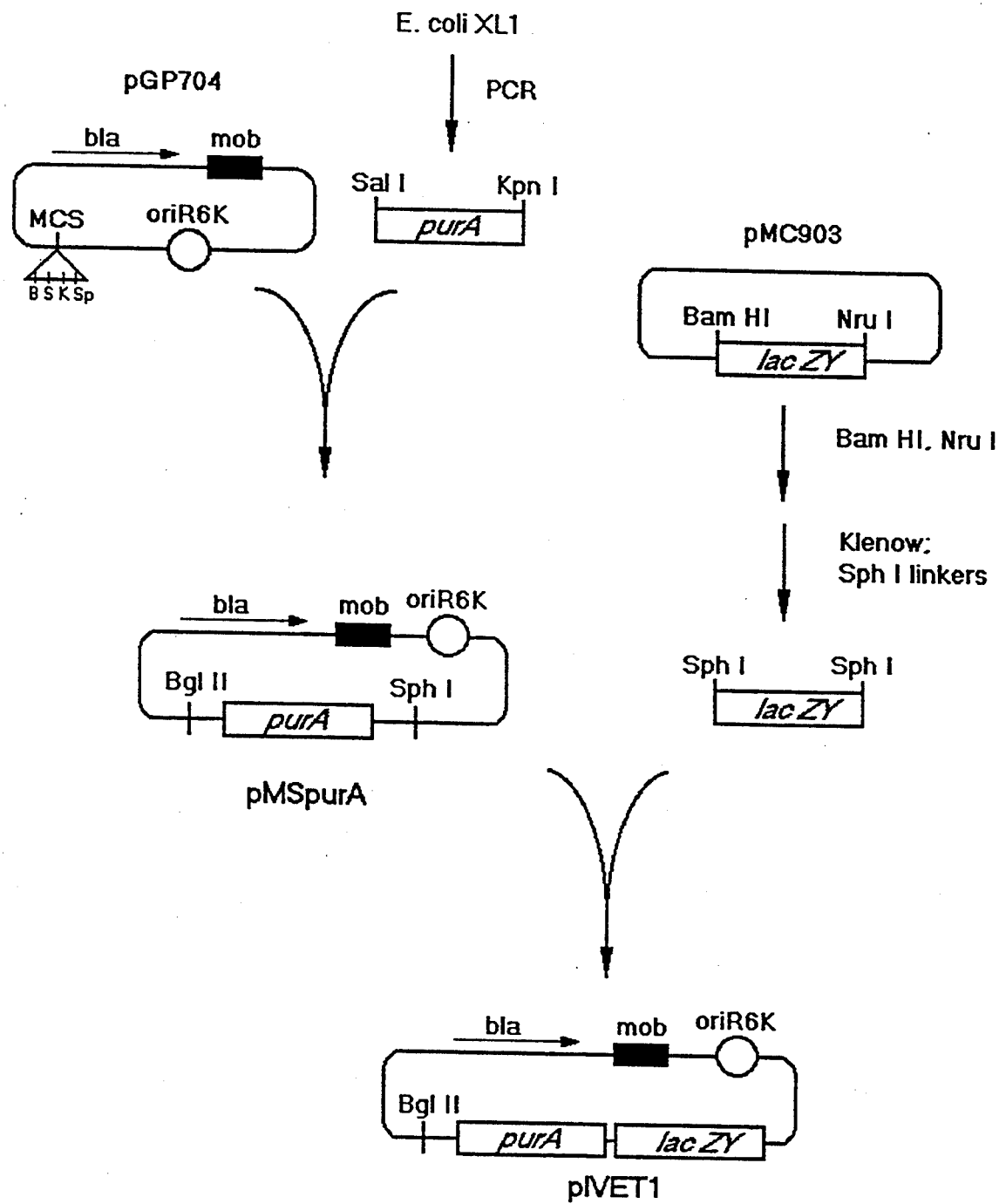
FIG. 5 is a diagrammatic representation of the construction of the pIVET1 vector.

The purA gene of *Salmonella typhimurium* encodes an enzyme for the synthesis of adenosine 5'-monophosphate (AMP). *S. typhimurium* strains deficient for the purA gene product are extremely attenuated in their ability to cause mouse typhoid or persist in animal tissues, (W. McFarland et al., *J. Microbiol. Patho.* 3, 129 (1987)). As shown in FIG. 5, a promoterless purA gene was obtained using the polymerase chain reaction (PCR; Perkin-Elmer Cetus) from the chromosome of *E. coli*, strain XL1, following the manufacture's instructions with modifications described in J. Slauch et al., *J. Bacteriol.* 173, 4039 (1991). *E.* coli strain XL1 (recA1 endA1 gyrA496 thi hsdR17 supE44 relA1 lac), was obtained from the *E. coli* Genetics Stock Center, Yale University, New Haven, Conn. The genotype of this strain is not. relevant except that it is purA+ and thyA+. The primers used for the PCR were 5'-GAATCCAgTcgacAGCAAACGGTG- 3', (SEQ ID NO: 1) and 5'-CAGGgGTACCAGAAT-TACGCGTC-3', (SEQ ID NO: 2). These sequences correspond to the sense strand from base pairs 468 to 491 and the anti-sense strand from base pairs 1814 to 1792, respectively, of the published sequence of the purA gene (S. Wolfe et al., *J. Biol. Chem.* 263, 19147 (1988)), with changes, denoted in lowercase letters, to introduce restriction sites near the amplified fragment. PCR was carried out in a buffer containing 2.0 mM $Mg^{2+}$ for 25 cycles of 1 minute at 94° C., 2 minutes at 55° C. and at 72° C. with a 5 second increment added to the 72° C. elongation step at every cycle. This procedure was carried out in a DNA Thermal Cycler #N801-0150 (Perkin-Elmer Cetus). The resulting purA-containing fragments were digested with Sal I (5'-end of purA) and Kpn I (3'-end of purA) (New England Biolabs), and ligated into the corresponding restriction site of the suicide vectors pGP704, V. Miller et al., *J. Bacteriol.* 170, 2575 (1988), available from Dr. J. Mekalanos Department of Microbiology and Molecular Genetics, Harvard Medical School, 200 Longwood Avenue, Boston, Mass. 02115 and Dr. V. DiRita Department of Microbiology and Immunology, University of Michigan Medical School, Ann Arbor, Michigan 48109, resulting in plasmid pMSpurA.

The promoterless lacZY operon, which serves the function of the reporter system, was obtained on a Barn HI, Nru I fragment of the plasmid pMC903 (M. Casadaban et al., *J. Bacteriol.* 143, 972 (1980). Restriction enzymes Barn HI and Nru I were obtained from New England Biolabs, and the digest followed the manufacturer's instructions. This lacZY restriction fragment contains the W205 trp-lac fusion that effectively removes the transcription start site of the lac operon, resulting in a $lacZ^+$, $lacY^+$ transcriptional fusion, (D. Mitchell et al., *J. Mol. Biol.* 93,331 (1975)). The ends of this restriction fragment were filled in with Klenow (New England Biolabs), (T. Maniatis, Molecular Cloning: A Laboratory Manual, Cold Spring Harbor Laboratory Press, Cold Spring Harbor, N.Y., 1989) followed by ligation to Sph I linkers (New England Biolabs). The ligation reaction followed the manufacturer's instructions. The resulting fragment was digested with Sph I (New England Biolabs) and cloned into the Sph I site of pMSpurA, 3' to the purA gene, resulting in pIVET1. The Bgl II site located 5' to the promoterless purI gene provides a convenient place to insert or clone random fragments of Sau3A I digested chromosomal DNA described in further detail below. The restriction enzymes Bgl II and Sau3 A I recognize palindromic sequences which are similar enough that when cleaved compatible extensions are produced.

Plasmid pIVET1 as constructed is a derivative of the broad host range suicide vector pGP704 that comprises the β-lactamase or bla gene which confers ampicillin resistance, a mobilization fragment or mob which contains the origin of transfer (ori T), thus, allowing for mobilization of pGP704, the origin of replication from plasmid R6K or oriR6K, and a multiple cloning site or polylinker. The R6K origin of replication (oriR6K) requires for its function a protein called Pi, which is encoded by the pir gene, which is supplied in trans by an *E. coli* strain SM10λ pir as discussed below.

Figure 6:
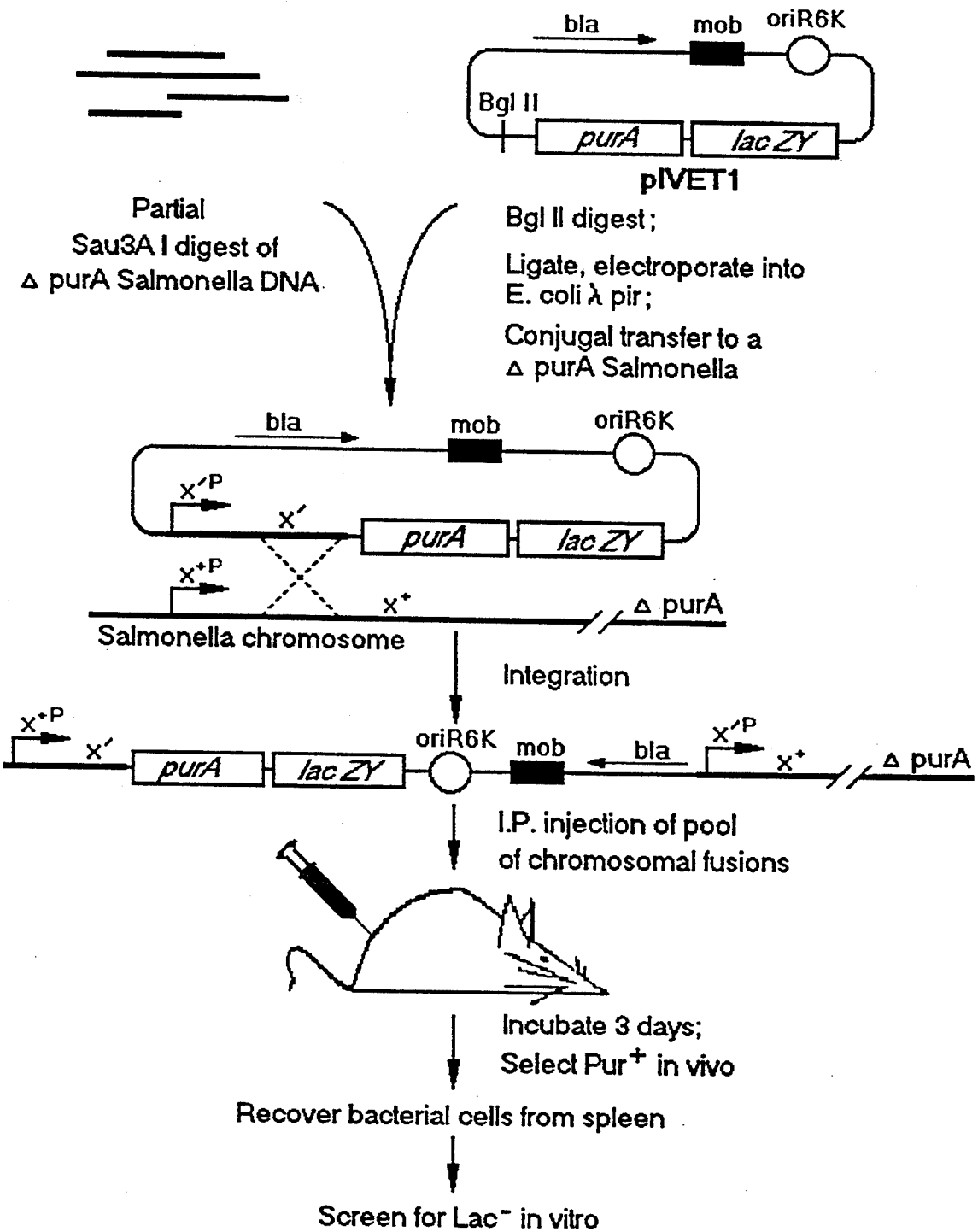
FIG. 6 is a flow sheet representing the method of selecting genes that are specifically induced in the host using the pIVET1 vector.

Method of Using the pIVET1 Vector for Selecting *S. typhirnurium* Genes that are Specifically Induced in Host Tissues Total genomic DNA was prepared from a purI deficient strain, MT168 (DEL 2901 [purI 874::IS10]), following the procedure set out by T. Manatis et al., Molecular Cloning: A .Laboratory Manual, Cold Spring Harbor Laboratory, Cold Spring Harbor, N.Y. Random chromosomal fragments having Sau3A I ends were then generated by partially digesting the previously isolated genomic DNA with Sau3A I (New England Biolabs) following the manufacturer's instructions. The deficient purA strain MT168 was obtained by standard Bochner selection methods. (Bochner et al., *J. Bacteriol.* 143, 926–933 (1980)). The exact genotypic nature of this strain is not important to the method of the present invention. It is the phenotypic nature of the strain MT168 and the fact that it is a non-reverting mutation or deficiency that is essential. As shown in FIG. 6 ligation of the Sau3A I DNA fragments with the pIVET1 vectors was achieved by standard methods producing the pIVET1 fusions. (T. Maniatis et al., Molecular Cloning: A Laboratory Manual, Cold Spring Harbor Laboratory, Cold Spring Harbor, N.Y.).

These pIVET1 fusions were then electroporated into competent *E. coli* cells from strain SM10λ pir (V . Miller et al., *J. Bacteriol.* 170, 2575 (1988) to create a pool of purA-lac fusions. *E. coli* SM10λ pir is available from Dr. J. Mekalanos Department of Microbiology and Molecular Genetics, Harvard Medical School, 200 Longwood Avenue, Boston, Mass. 02115 and Dr. V. DiRita Department of Microbiology and Immunology, University of Michigan Medical School, Ann Arbor, Mich. 48109.

Electroporation was carried out with a BioRad Gene Pulser apparatus Model No. 1652098. *E. coli* SM 10λ pir cells were prepared for electroporation as per the manufacturer's instructions. An aliquot of cells was mixed with an aliquot of pIVET1 fusions and placed on ice for 1 minute. The mixture was transferred into a cuvette-electrode (1.9 cm) and pulsed once at a field strength of 12.5 kV/cm as per manufactures instructions. The mixture was then added to 1 ml SOC medium (2% tryptone, 0.5% yeast extract, 10 mM NaCl, 25 mM KCl, 10 mM $MgCl_2$, 10 mM $MgSO_4$, 20 mM glucose) and shaken at 37° C. for 2-3 hours.

Figure 7:
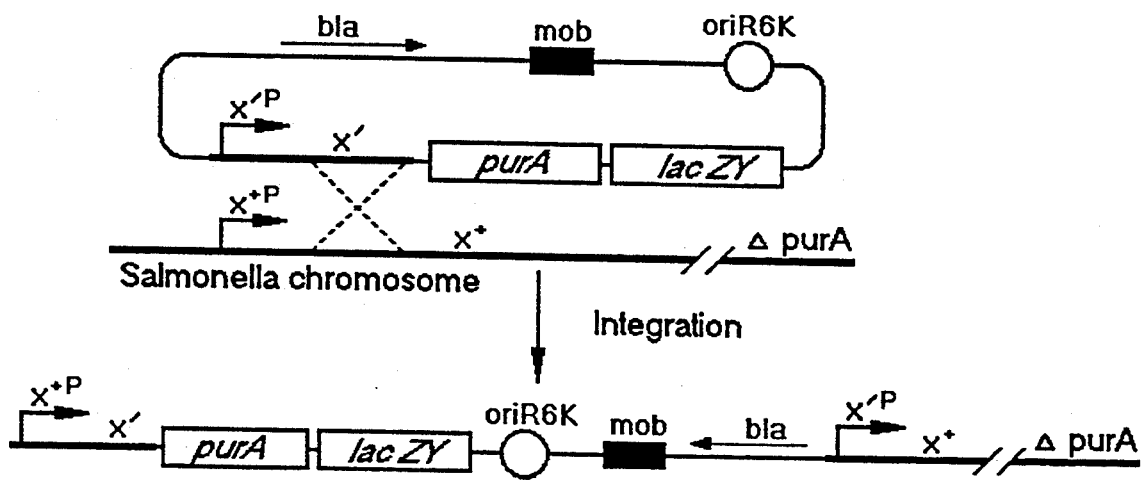
FIG. 7 is a diagramatic representation of the homologous recombination event which occurs between the pIVET1 fusion and the S. typhimurium chromosome.

The transformed *E. coli SM*10λ pir cells were then used to introduce the pIVET1 fusions, by way of conjugation, into *S. typhimurium*, strain MT 168, which also lacks the pir gene following the procedures described by J. Miller, A Short Course in Bacterial Genetics: a laboratory manual and handbook for *Escherichia coli* and related bacteria., Cold Spring Harbor Press, Cold Spring Harbor, N.Y., (1992). 50 μg/ml of ampicillin was then added to the culture. Those *S. typhimurium* which survive in the presence of ampicillin must have the pIVET1 fusion integrated into their genome by way of homologous recombination with the cloned Sau3A I Salmonella DNA. This results in single copy diploid fusions in which one promoter drives the expression of the purA-lac fusion and the other promoter drives the expression of the wild type gene, (FIG. 7).

There are several important points about this integration event. First, the cloned Sau3A 1 chromosomal fragments provide the only site of homology for integration into the recipient chromosome. The purA gene was obtained by PCR from an *E. coli* chromosome, as discussed above, and *E. coli* and *S. typhimurium* chromosomes are sufficiently divergent to prevent recombination, (H. Ochman et al., in *Escherichia coli* and *Salmonella typhimurium*: cellular and molecular biology, F. C. Neidhart, Ed. American Society for Microbiology, Washington D.C. (1987)). Also, *S. typhimurium* does not contain a lac operon. Second, only those clones that contain the 5'-end of the gene of interest, i.e., the promoter, will generate both a functional fusion and a duplication that maintains transcription of the wild type gene. Other types of clones will not result in the desired product. For example, those constructs that contain an internal fragment of the gene will generate a fusion, encoded by the synthetic operon, under the appropriate regulation, but will disrupt the expression of the wild type gene. This type of construct can potentially be selected against in the animal if the product of the wild type gene, is required for the infection process. In other cases, the promotor will not be in the proper orientation to drive the expression of purA. Therefore, integration of the cloned fragment into the chromosome does not result in a functional fusion.

The pattern of lacZ expression in a random pool of fusion strains was assessed in vitro on MacConkey Lactose indicator medium (Difco Laboratories). The level of lacZ expression required to give a Lac+ phenotype appeared to correspond to the level of purA expression required to supplement the parental PurA auxotrophy; that is, colonies that were Lac+ (red) on MacConkey Lactose indicator medium were Pur+ on minimal medium; colonies that were Lac± (pink) were semi-auxotrophic on minimal medium; and colonies that were Lac− (white) were Pur− on minimal medium. Of the preselected fusion strains, 33% (116/346) were Lac+, 16% (56/346) were Lac±, and 50% (174/346) were Lac−. This indicates that before selection in the mouse, only 33% of the fusion strains displayed sufficient in vitro expression to result in both a Lac+ and a Pur+ phenotype.

A BALB/c mouse (Charles River Laboratories) was injected intraperitoneally with approximately $10^6$ cells of the pool of integrated purA-lac fusion strains. Three days after infection, the mouse was sacrificed and its spleen, one of the major sites of systemic infection for *S. typhimurium*, was removed and homogenized in 2 ml of sterile saline. The homogenate was grown overnight in LB having ampicillin and $10^6$ cells were injected into a second mouse, where the process is repeated.

Only bacteria that expressed purA at high enough levels to overcome the parental purine deficiency of the auxotroph should have survived and multiplied in the mouse. Indeed, the bacterial cells recovered from the spleen and plated out on MacConkey Lactose indicator medium had an increased percentage of cells that were Lac+ (and therefore PurA+) compared to the preselected fusion strains or the initial inoculum: 86% (235/273) of the bacterial cells recovered from the spleen were Lac+ (red), 9% (24/273) were Lac± (pink), and 5% (14/273) were Lac− (white). Such a shift toward Lac+ cells was consistent with the selection of strains that contain fusions to promoters that are transcriptionally active in vivo. Observation of this so called "red shift", i.e., 33 % being Lac+ in the initial inoculum shifting towards 86% being Lac+ recovered from the spleen, is the only indication that the selection took place. This is important for any IVET selection and exemplifies the importance of the lacZY operon in the system. The various parameters that affect any given selection, e.g., the length of incubation time in the host, or the number of times the pool is taken through the selection, should be determined empirically with the success of the selection monitored by the red shift.

It should be noted that the level of Lac activity in fusions constructed with vectors other than pIVET1 may not coincide with the activity of the gene that is the bases of the selection. That is, the profile of Lac+ to Lac− in the post-selected pool will vary depending on the pIVET vector. In this regard, the red shift observed after selection with other vectors may be more or less than that observed with pIVET1. However, the genes that presumably show the greatest in vivo induction are still those that have the least transcriptional activity in vitro. In those cases where the host-selected pool still has a significant number of white colonies on MacConkey medium, it may be necessary to screen for Lac activity using a different assay medium, such as one that contains the chromogenic substrate X-gal. In this case, one observes a "blue shift" after passage through the host, where the fusions that are the lightest blue among the blue-shifted survivors are the fusions of interest (i.e., those fusions that show the greatest in vivo induction).

Figure 8:
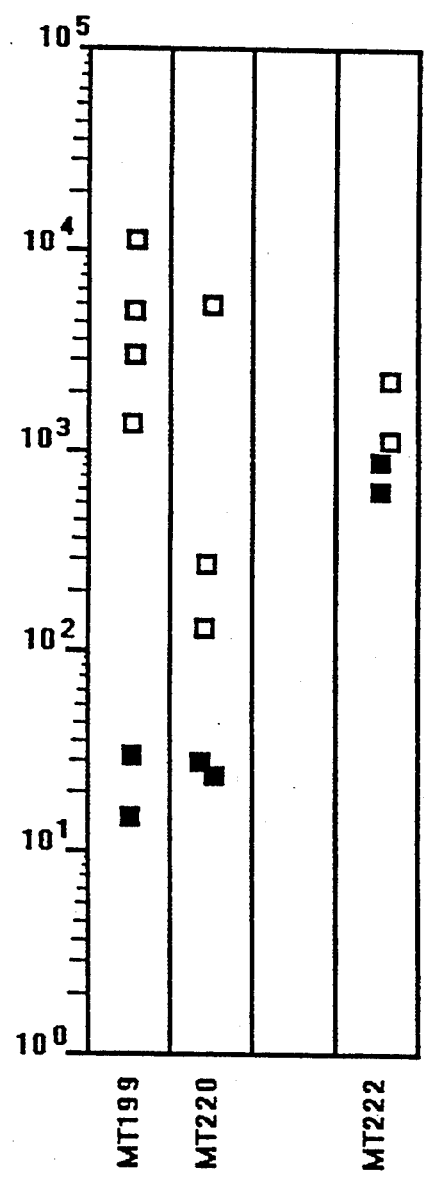
FIG. 8 is a comparison of $\beta$-galactosidase ($\beta$-gal) expression from bacterial cells that were recovered from mouse spleen versus the same strain grown on rich media. The vertical axis depicts the picounits of $\beta$-gal per colony-forming unit, where units of $\beta$-gal equal micromoles of o-nitrophenol (ONP) formed per minute. The open boxes denotes the $\beta$-gal activity of cells recovered from the spleen. The closed boxes denote the $\beta$-gal activity from cells grown overnight in rich medium.

To confirm that these fusions were specifically induced in vivo, the β-galactosidase activity in bacteria recovered from the spleens of infected mice was measured and compared to the β-galactosidase activity measured for the same strain grown overnight in rich medium, as shown in FIG. 8. Individual Lac⁻ or white colonies were picked from the bacterial cells isolated from the spleen and growing on MacConkey indicator medium. Each individual strain was grown in 2 ml of LB overnight at 37° C. Each overnight culture, approximately $10^5$ organisms, was injected intraperioneally into individual BALB/c mice. After six days the mice were sacrificed and their spleens were removed and individually homogenized in 2 ml of sterile saline. Each sample was centrifuged for 2 minutes at 12,000×g and the supernatant was discarded. The pellet, containing both bacterial and splenic cells, was resuspended in 1 ml sterile deionized water and vortexed, lysing the eukaryotic cells. The sample was incubated with DNase I (Boehringer Mannheim) for 20 minutes at room temperature, centrifuged for 2 minutes at 12,00×g, and the supernatant was discarded. The pellet, containing the bacterial cells, was washed twice with 1 ml Z buffer (J. H. Miller, "Experiments in Molecular Genetics," Cold Spring Harbor Laboratory Press (1972)), and resuspended in 400 μl of Z buffer.

The bacterial cells were permeabilized by addition of 50 μl of 1% sodium dodecyl sulfate and 50 μl of chloroform. The activity of each sample of bacterial cells was determined by kinetic assay, using fluorescent substrate fluorescein di-β-D-galactopyranoside (FDG; Molecular Probes, Inc.) and a model SPF-500c spectrofluorometer (SLM Instruments, Inc.) as per the manufacturer's instructions. The activity is reported per colony forming unit (cfu) in the bacterial suspension. The units of β-galactosidase were obtained by comparing the activity to a standard curve determined with the purchased β-galactosidase (Sigma). The units of this purified enzyme were designated by the manufacturer and are defined as μmoles of o-nitrophenol formed per minute, using o-nitrophenyl-galactopyranoside as substrate. Although there is tremendous mouse to mouse variability in this assay, it can be seen that fusions to the in vivo induced genes, are highly induced in animal tissues relative to the fusion strains grown in laboratory media. As a control for this experiment, a random Lac+ fusion strain, MT222, from the preselected pool was chosen. The fusion in this strain is not significantly induced in animal tissues compared to growth in laboratory medium; the fusion is highly expressed in both conditions.

Identifying the In Vivo Induced Genes

In order to identify the in vivo induced genes, a genetic approach to clone the 15 selected in vivo induced fusions directly from the bacterial chromosome by phage P22 transduction was developed. Briefly, a bacteriophage P22 lysate is made on the fusion strain of interest and used to transduce a recipient strain that contains the replication protein, Pi, which is required for autonomous replication of pIVET1. Presumably, after introduction of the chromosomal fragment containing the integrated fusion construct, the plasmid circularizes by homologous recombination at the region of duplication defined by the cloned S. typhimurium DNA. The circularized fragment can then replicate as a plasmid in the presence of the Pi replication protein, resulting in the cloned fusion of interest. In other organisms where cloning by transduction is not possible, the fusions can be cloned by more standard methods (S. Berger et al., Guide to Molecular Cloning Techniques, Academic Press, Inc. 1987).

Using a primer homologous to the 5'-end of the purl gene approximately 200 to 400 base pairs of S. typhimurium DNA were sequenced (United States Biochemical) immediately upstream or 5 ' to the purA gene in each of the cloned fusions. Sequence analysis indicates that the 15 fusions represent five different genes. Two of five fusions are in genes that show no significant homology to sequences in GenBank version 72, (J. Devereux et al., Nucleic Acids Res. 12, 387 (1984)). This suggests that the in vivo expression technology (IVET) system of the present invention has identified previously uncharacterized genes that are specifically induced during mouse infection.

One fusion to a known sequence was to the carAB operon, whose genes encode the two subunits of carbamoyl-phosphate synthetase. This enzyme is involved in arginine and pyrimidine biosynthesis, (J. Piette et al., Proc. Natl. Acad. Sci. U.S.A. 81, 4134 (1984), H. Nyunoya et al., Proc. Natl. Acad. Sci. U.S.A. 80, 4629 (1983), and N. Glandsorff, in Escherichia coli and Salmonella typhimurium: Cellular and Molecular Biology, F. Neidhart, Ed.(American Society for Microbiology, Washington, DC, 1987), pp 321-344). The induction of this operon is consistent with the apparent low availability of pyrimidines in animal tissues, (P. Fields et al., Proc. Natl. Acad. Sci. U.S.A. 83, 5189 (1986)). Thus, the IVET selection of the present invention allows the identification of those products involved in intermediary metabolism and whose induction in vivo is necessary for virulence and survival in animal tissues. The second fusion is located in the pheST himA operon that encodes the two subunits of phenylalanyl-tRNA synthetase and one subunit of integration host factor (IHF), which is a DNA binding protein involved in DNA replication, gene regulation and site-specific DNA recombination (R. Leunk et al., Infect. Immun. 36, 1168 (1982), and H. Lockman et at., Infect. Immun. 60, 491 (1992)). It is not known why the genes for phenylalanyl-tRNA synthetase and a subunit of IHF are transcribed together; therefore, it is not clear whether induction of this operon in vivo is in response to a depletion in charged tRNA or a demand for an increased level of IHF for some regulatory function. Changes in type I pilin expression, dependent on IHF, (C. Dorman et al., J. Bacteriol. 169, 3840 (1987)), do confer an advantage to S. typhimurium in preventing clearance from animal tissues (R. Leunk et al., Infect. Immun. 36, 1168 (1982) and H. Lockman et al., Infect. Immun. 60, 491 (1992)).

The third known fusion is in the rfb operon, which encodes approximately 20 genes involved in O-antigen synthesis, the outermost layer of lipopolysaccharide (P. Mäkelä et al. Handbook of Endotoxin: Chemistry of Endotoxin, E. T. Rietschel, Ed. (Elsevier, N.Y., 1984), Vol. 1 pp. 59-137; and X. Jiang, Mol. Microbiol. 5, 695 (1991)). This fusion is located in the penultimate gene of the operon. However, the direction of transcription is in the opposite orientation to that of the rfb operon and would generate an antisense transcript to the rfb operon complementary to at least the 3'-end of the rib mRNA. Currently, experiments are being conducted to determine whether this in vivo induced transcript may act through an antisense mechanism to down-regulate O-antigen synthesis in vivo. Mutants defective in O-antigen synthesis are highly attenuated when delivered orally but are fully virulent when delivered intraperitoneally (N. Nnalue et at., *Infect. Immun.* 58, 2493 (1990)).

To determine the overall contribution of in vivo induced genes to *S. typhimurium* pathogenesis, mutant strains defective in in vivo induced expression have been constructed. Using the sensitive chromogenic substrate 5-bromo-4-chloro-3-indolyl-$\beta$-D-galactopyranosicle (X-gal) in association with transposon mutagenesis, Mud-Cm insertion elements in the cloned in vivo induced operons have been isolated. These transposons disrupt the gene at the site of insertion and furthermore reduce the expression of downstream genes in the same operon by polarity. Thus, the insertions decrease the expression of lacZ, shifting the colony color from blue (higher levels of expression) to light blue (lower levels of expression) on medium containing X-gal.

The effect of reduced in vivo induced expression on virulence was determined by crossing the insertion mutations into an otherwise wild-type chromosome and orally challenging BALB/c mice with the resultant mutant strains. The oral lethal dose of those insertion-bearing strains required to kill 50% of infected animals (LD$_{50}$) for wild-type infection of a BALB/c mouse is $10^4$ cells. Insertions in all three operons tested caused an increase in the LD$_{50}$ from 200−to >2×$10^4$ fold. This indicates that the method of the present invention selects for genes that are important for *S. typhimurium* virulence. Furthermore, mice immunized with these attenuated strains were tested to determine whether they were resistant to oral challenge with wild-type *S. typhimurium*. Six out of thirteen mice previously orally immunized with MT220 (iviII-7::Mud-Cm) survived an oral challenge of wild-type organisms at a dose $10^5$-fold above the LD$_{50}$, whereas 0 out of 15 control mice survived a challenge at this dose. This result suggests that the in vivo selection of the present invention provides a means of isolating attenuated mutants that may have utility as live vaccine strains.

Because purine auxotrophy attenuates many pathogenic bacteria (W. McFarland et al., *J. Microbiol. Pathol.* 3, 129 (1987); V. Baselski et al., *Mol. Microbio.* 22, 181 (1978); G. Ivanovics et al., *J. Bacteriol.* 85 147 (1968); H. Levine et al., *J. Immunol.* 81,433 (1958); and S. Straley et al., *Infect. Immun.* 45, 649 (1984)), the IVET selection system of the present invention should be of general use in a variety of bacterial-host systems. Also, several other biosynthetic genes can in theory be used in this selection scheme for a variety of pathogenic microorganisms as described below in the following example.

EXAMPLE 2

Construction of the pIVET2 Vector

The thyA gene encodes an enzyme for the synthesis of thymidylate synthase. Microorganisms which are deficient for the thyA gene product are resistant to the antibiotic trimethoprim, while microorganisms having a functional copy of the thyA gene are sensitive to trimethoprim. A promoterless thyA gene was obtained using the polymerase chain reaction (PCR; Perkin-Elmer Cetus) from the chromosome of *E. coli*, strain XL1, following the manufacturer's instructions with modification described in J. Slauch et al., *J. Bacteriol.* 173, 4039 (1991). The primers used for the PCR were 5'-AGCAACAGgTaCCTGAGGAACCATG-3' (SEQ ID NO:3) and 5'-TGGCAGGATGaaTtcTTAGATAGCCACC-3' (SEQ ID NO:4. These sequences correspond to the sense strand from base pairs 192 to 217 and the anti-sense strand from base pairs 1027 to 997, respectively, of the published sequence of the thyA gene (M. Belfort et al., *Proc. Natl. Acad Sci.* U.S.A. 80, 4914 (1983)), with changes, denoted in lowercase letters, to introduce restriction sites near the ends of the amplified fragment. PCR was carried out in a buffer containing 2.0 mM $Mg^{2+}$ for 25 cycles of 1 minute at 94° C, 2 minutes at 55° C. and 3 minutes at 72° C. with a 5 second increment added to the 72° C. elongation step at every cycle. This procedure was carried out in a DNA Thermal Cycler #N801-0150 (Perkin-Elmer Cetus). The resulting thyA-containing fragment were digested according to manufacturer's instructions with EcoR I (5'-end of thyA) and Kpn I (3'-end of thyA) (New England Biolabs), and ligated into the corresponding site of pGP704, resulting in plasmid pMSthyA, (not shown).

The promoterless lacZY operon is isolated and linked to the thyA fragment following the same procedures as discussed in Example 1 for linking the lacZY operon to the purA gene.

Method of Using the pIVET2 Vector for Selecting *V. cholerae* Genes that are Specifically Induced in Host Tissues Total genomic DNA was prepared from a *V. cholerae* thyA deficient strain, MT173 following the procedure set out by T. Maniatis et al., Molecular Cloning: A Laboratory. Manual, Cold Spring Harbor Laboratory, Cold Spring Harbor, N.Y. Random chromosomal fragments having Sau3A I ends were then generated by partially digesting the previously isolated genomic DNA with Sau3A I (New England Biolabs) following the manufacturer's instructions. The deficient thyA strain MT173 (0 395 thyA) was obtained by selection for trimethoprim resistance (J. H. Miller, "Experiments in Molecular Genetics," Cold Spring Harbor Laboratory Press (1972)). The exact genotypic nature of this strain is not important to the method of the present invention. It is the phenotypic nature of the strain MT173 and the fact that it is a non-reverting mutation or deficiency that is essential for virulence. Ligation of the resulting Sau3A I DNA fragments with the pIVET2 vector was achieved by standard methods, (T. Maniatis et al., Molecular Cloning: A Laboratory Manual, Cold Spring Harbor Laboratory, Cold Spring Harbor, N.Y.) producing a pIVET2 fusion.

These pIVET2 fusions were then electroporated into competent *E. coli* cells from strain SM10 pir to create a pool of thyA-lac fusions, following the procedures described in Example 1.

The transformed *E. coli* SM10λ pir cells were then used to introduce the pIVET2 ; fusion into *V. cholerae*, strain MT173, which also lacks the pir gene following the procedures referenced in Example 1. 50 μg/ml of ampicillin was then added to the culture. Those *V. cholerae* which survive in the presence of ampicillin must have the pIVET2 fusion integrated into their genome by way of homologous recombination with the cloned Sau3A I *V. cholerae* DNA. This results in single copy diploid fusions in which one promoter drives the expression of the thyA-lac fusion and the other promoter drives the expression of the wild type gene.

The pattern of LacZ expression in a random pool of fusion strains was assessed in vitro on MacConkey Lactose indicator medium (Difco Laboratories). Of the preselected fusion strains, 13% were (28/184) Lac+, and 87% (156/184) were Lac−. This indicates that before selection in the mouse, only 13% of the fusion strains displayed sufficient in vitro expression to result in both a Lac+ and a trimethoprim sensitive phenotype.

The resulting pool of integrated thyA-lac fusion strains of approximately $10^6$ cells is used to infect 5 day old CD1 mice by oral infection. Three days after infection, the mouse is sacrificed and its intestine, the major site of infection for *V. cholerae* is removed and homogenized in 2 ml of sterile saline. The bacteria are isolated from the intestinal homogenate in the same manner as they are isolated from the splenic cells in Example 1. One advantage of the thyA system is its ability to select thyA− routants with the antibiotic trimethoprim. Thus, the thyA system allows positive selection for fusion genes that are both induced in vivo (by selecting Thy+) and transcriptionally inactive in vitro Coy selecting Thy−) or those colonies which are trimethoprin resistant.

Only bacteria that expressed thyA at a high enough levels to overcome the parental thymine deficiency should have survived and multiplied in the mouse. Indeed, the bacterial cells recovered from the intestine had an increased percentage of cells that were Lac+ (and therefore thy+) compared to the preselected fusion strains or the initial inoculum: 54% (63/117) of the bacterial cells recovered from the intestine were Lac+ (red), and 46% (54/117) were Lac− (white). Such a "red shift" toward Lac+ cells was consistent with the selection of strains that contain fusions to promoters that are transcriptionally active in vivo. Observation of this so-called red shift, i.e., 13% being Lac+ in the initial inoculum shifting towards 54% being Lac+ recovered from the intenstine, is the only clear indication that the selection took place.

EXAMPLE 3

Construction of the pIVET8 Vector

In addition to pIVET systems based on complementation of biosynthetic genes, vectors have been constructed based on drug resistance. The CAT gene from plasmid pCM1 (Pharmacia LKB Biotechnology) encodes an enzyme chloramphenicol acetyl transferase. *S. typhimurium* strains having the CAT gene are resistant to the antibiotic chloramphenicol (cm). A promoterless CAT gene was obtained by digesting pCM1 with Sal I (New England Biolabs) according to the manufacturer's instructions. The resulting CAT-containing fragments having Sal I ends were ligated into the corresponding restriction site of suicide vector pGP704, as discussed prior in Example 1, resulting in plasmid pMScat. The promoterless lacZY operon, which serves the function of the reporter system, was obtained on a Bam HI, Nru I fragment of the plasmid pMC903 as discussed previously in Example 1. The ends of this restriction fragment were filled in with Klenow followed by ligation to Sph I linkers, as discussed previously in Example 1. The resulting lacZY fragments were digested with Sph I (New England Biolabs) and cloned into the Sph I site of pMScat, 3′ to the CAT gene, resulting in pIVET8. The Bgl II site located 5′ to the promoterless CAT gene provides a convenient place to insert or clone random fragments of Sau3A I digested chromosomal DNA.

Method of Using the pIVET8 Vector for Selecting *S. typhimurium* Genes that are Specifically Induced in Host Tissues or in Macrophage Tissue Cultures Total genomic DNA was prepared from a *S. typhimurium* wild type strain MT110 having a spontaneous streptomycin resistant mutation following the procedures set out by T. Maniatis et al., Molecular Cloning: A Laboratory Manual, Cold Spring Harbor Laboratory, Cold Spring Harbor, N.Y. Random chromosomal fragments having Sau3A I ends were then generated by partally digesting the previously isolated genomic DNA with Sau3A I (New England Biolabs) following the manufacturer's instructions. Ligation of the Sau3A I DNA fragment into the Bgl II site of the pIVET8 vector was achieved by standard methods as discussed in Example 1.

These pIVET8 fusions were then electroporated into competent *E. coli* cells from strain SM10λ pir to create a pool of cat-lac fusions, following the procedures set out in Example 1. The transformed *E. coli* SM10λ), pir cells were then used to introduce the pIVET8 fusion into *S. typhimurium*, strain MT110, which also lacks the pir gene following the procedures referenced in Example 1. 50 μg/ml of ampicillin was then added to the culture. Those *S. typhimurium* or cat-lac fusion strains which survive in the presence of ampicillin must have the pIVET8 fusion integrated into their genome by homologous recombination with the cloned Sau3A I Salmonella DNA. This results in single copy diploid fusions in which one promoter drives the expression of the cat-lac fusion and the other promoter drives the expression of the wild type gene.

The pattern of lacZ expression in a random pool of cat-lac fusion strains was assessed in vitro on MacConkey Lactose indicator medium (Difco Laboratories). Of the preselected fusion strains 21% (37/180) were Lac+ and 79% (143/180) were Lac−. This indicates that before selection in the mouse, only 21% of the fusion strains displayed sufficient in vitro expression to result in both a Lac+ and chloramphenicol resistant phenotype.

A BALB/c mouse (Charles River Laboratories) was injected intraperitoneally with approximately $10^6$ cells of the pool of integrated cat-lac fusions. Intraperitoneal injections of 0.2 mls of 0.09 mg chloramphenicol (Sigma) were made twice daily in addition to the 2.5 mg/ml of chloramphenicol which was added to the drinking water. Three days after infection, the mouse was sacrificed and it's spleen was removed. The bacterial cells were isolated in the same manner as in Example 1. The recovered cells were injected into a second mouse where the process was repeated. It is important to note that the amount of chloramphenicol administered was determined empirically, that is, by noticing the red shift obtained in the bacterial population obtained after chloramphenicol treatment.

Only bacteria that expressed CAT at a high enough level to overcome the sensitivity to chloramphenicol should have survived and multiplied in the mouse. Indeed, the bacterial cells recovered from the spleen had an increased percentage of cells that were Lac+ (and therefore chloramphenicol resistant) compared to the initial inoculum or the preselected fusion strains. 5% (184/193) of the bacterial cells recovered from the spleen were Lac+ (red), and 5% (9/193) were Lac−(-white) such a shift toward Lac+ cells was consistent with the selection process of strains that contain fusions to promoters that are transcriptionally active in vivo. Again, observation of this red shift, i.e., 21% being Lac+ in the initial inoculum shifting towards 95% being Lac+ recovered from the spleen, indicates that selection took place.

A second method for selecting in vivo induced genes is to incubate *S. typhimurium* cat-lac fusions with $10^7$ RAW tissue culture macrophages for two to three hours. RAW tissue cultures were obtained from Dr. John Collier, and Dr. Phil Hanna, Department of Microbiology and Molecular Genetics, Harvard Medical School, 200 Longwood Avenue, Boston, Mass. 02115. The tissue culture is then washed three times with Earle's tissue culture medium with 10% fetal calf serum (Gibco Laboratories). The macrophage cells are then incubated with 100 μg/ml gentamicin for two hours to kill any extracellular Salmonella. Gentamicin does not penetrate mammalian cells; therefore Salmonella that have invaded the macrophage cells will not be exposed to the gentamicin. Again, the tissue culture cells are washed three times with tissue culture medium followed by a 16 hour incubation in the presence of chloramphenicol. The tissue culture is again washed three times with a tissue culture medium, whereby the infected macrophage are then incubated in 1 ml sterile water to lyse the macrophages. The bacterial cat-lac fusions are again incubated with $10^7$ RAW tissue culture macrophages and the process is repeated.

Only bacteria that expressed CAT at a high enough level to overcome the sensitivity to chloramphenicol should have survived and multiplied in the macrophage cells. Indeed, the bacterial cells recovered from the spleen had an increased percentage of cells that were Lac+ and therefore chloramphenicol resistant compared to the preselected fusion strains or the initial inoculum: 86% (25/29) of the bacterial cells recovered from the macrophage were Lac+ (red), and 14 % (4/29) were Lac− (white). Such a shift toward Lac+ cells was consistent with the selection process of strains that contain fusions to promoters that are transcriptionally active in vivo. Again, observation of this red shift, i.e., 21% being Lac+ in the initial inoculum shifting towards 86% being Lac+ recovered from the macrophage tissue culture, indicates that the selection took place.

The forgoing description is considered as illustrative only of the principals of the invention. Furthermore, since numerous modifications and changes will readily occur to those skilled in the art, it is not desired to limit the invention to the exact construction and processes shown as described above. Accordingly, all suitable modifications and equivalents may be restored to falling within the scope of the invention as defined by the claims which follow.

---

The embodiments of the invention in which an exclusive property or privilege is claimed are defined as follows:

1. A selection method for the identification of one or more genes of a pathogenic microorganism, said gene(s) being specifically induced within host tissue during in vivo infection of a host, comprising the steps of:
   (a) constructing a pool of fusion strains wherein a library of expression plasmids is integrated by homologous recombination into the genome of cells of said pathogenic microorganism, the library containing a pool of chromosomal fragments collectively representing the pathogenic microorganisms's genome, wherein each expression plasmid contains a chromosomal fragment from said pool of chromosomal fragments, wherein said pathogenic microorganism is either:
      (1) an auxotrophic mutant strain of said pathogenic microorganism, wherein the auxotrophic mutation is a deletion or nonreverting mutation of a gene which is necessary for the microorganism's growth in vivo in said host, or
      (2) a strain of said pathogenic microorganisms sensitive to a first antibiotic, and
   wherein said expression plasmid comprises:
      (1) a gene conferring resistance to a second antibiotic,
      (2) a promoterless synthetic operon comprising two genes, wherein the first gene complements the mutation of the pathogenic microorganism or confers resistance to the first antibiotic, and the second gene functions as a reporter gene, and
      (3) a cloning site 5' to the synthetic operon containing said chromosomal fragment, wherein the chromosomal fragment provides the only region of said expression plasmid capable of homologous recombination with the genome of the pathogenic microorganism;
   (b) infecting said host with the pool of fusion strains resulting from step (a), and further treating said host with said first antibiotic if said first gene of the synthetic operon confers resistance;
   (c) harvesting from said host the fusion strains that survive and propagate in the host after step (b);
   (d) plating said harvested fusion strains of step (c) on a medium that detects expression of said reporter gene; and
   (e) picking those fusion strains which fail to express said reporter gene in vitro, thereby identifying strains which contain an expression plasmid integrated into a gene which is specifically induced within host tissue during in vivo infection.

2. A selection method for the identification of one or more genes of a pathogenic microorganisim, said gene(s) specifically induced within host tissue during in vivo infection of a host, comprising the steps of:
   (a) isolating a fragmenting total chromosomal DNA of a first microbial strain, wherein said first strain is either:
      (1) an auxotrophic mutant strain of said pathogenic microorganism, wherein the auxotrophic mutation is a deletion or a nonreverting mutation of a gene which is necessary for the microorganism's growth in said host, or
      (2) a strain of said pathogenic microorganism sensitive to a first antibiotic;
   (b) cloning the chromasomal fragments resulting from step (a) into a suicide expression plasmid to create library of pIVET fusion plasmids, wherein said suicide expression plasmid comprises;
      (1) a gene conferring resistance to a second antibiotic,
      (2) a promoterless synthetic operon comprising a first gene which complements the mutation of the first microbial strain or confers resistance to the first antibiotic, and a second sequence which functions as a reporter gene, and (3) a cloning site 5' to the synthetic operon, wherein said cloning step fuses a chromosomal fragment to the 5' end of the promoterless synthetic operon, and wherein the chromosomal fragment provides the only region of the pIVET fusion plasmid capable of homologous recombination with the genome of the first microbial strain;

(c) amplifying the library of pIVET fusion plasmids resulting from step (b) by introducing the plasmids into a second microbial strain which provides a replication protein required for autonomous replication of said plasmids;

(d) transferring the library of pIVET fusion plasmids into cells of the first microbial strain, under conditions where the pIVET fusion plasmids may integrate by homologous recombination at the site of homology provided by the cloned chromosomal fragments and where said plasmids fail to autonomously replicate, to create a pool of fusion strains;

(e) exposing the pool of fusion strains resulting from step (d) to said second antibiotic, to select a pool of fusion strains exhibiting integration by homologous recombination;

(f) infecting said host with the pool of selected fusion strains resulting from step (e), and further treating said host with said first antibiotic if said first gene of the synthetic operon confers resistance;

(g) harvesting from said host the fusion strains that survive and propagate in the host after step (f);

(h) plating said harvested fusion strains of step (g) on a medium that detects expression of said reporter gene; and (i) picking those fusion strains which fail to express said reporter gene in vitro, thereby identifying strains which contain a pIVET fusion plasmid integrated into a gene which is specifically induced within host tissue during in vivo infection.

3. The method of claim 2, wherein said second antibiotic is ampicillin and wherein the gene conferring resistance to a second antibiotic in step (b) is the β-lactamase (bla) gene.

4. The method of claim 2, wherein said first strain is an auxotrophic mutant and wherein the first gene in the synthetic operon of step (b) complements the auxotrophic mutation of the first microbial strain.

5. The method of claim 2, wherein said first strain is sensitive to a first antibiotic, and wherein the first gene in the synthetic operon of step (b) confers resistance to the first antibiotic.

6. The method of claim 5, wherein said first antibiotic is chloramphenicol, and said first gene is a chloramphenicol acetyl transferase (CAT) gene.

7. The method of claim 2, wherein said second microbial strain of step (c) a strain of *E. coli* providing a Pi replication protein.

8. The method of claim 2, wherein the transfer of step (d) is performed by a method selected from the group consisting of transduction, transformation, electroporation, and conjugation.

9. The method of claim 2, further comprising the step of screening said pool of selected fusion strains of step (e) to determine the percentage of fusion strains which express the reporter gene in vitro prior to infection of a host.

10. The method of claim 9, further comprising the step of screening said plated fusion strains of step (h) to determine the percentage of fusion strains which express the reporter gene in vitro subsequent to infection of a host and comparing the obtained percentage to the percentage obtained in step (e).

11. The method of claim 2, wherein said steps (f) and (g) are repeated.

12. The method of claim 2, further comprising the step of isolating, from a fusion strain picked in step (i), the chromosomal fragment containing the integrated pIVET fusion plasmid, said fragment comprising the identified gene.

13. The method of claim 12, further comprising the step of determining the overall contribution of the identified in vivo host induced gene to the pathogenesis of said pathogenic microorganism by constructing a mutant strain of said pathogenic microorganism that is defective in the identified in vivo host induced gene and challenging said host with said mutant strain.

14. The method of claim 2, wherein said pathogenic microorganism is a bacterium.

15. The method of claim 2, wherein said sequence which functions as a reporter gene encodes a protein, the expression of which is assessable in vitro.

16. The method of claim 15, wherein said sequence is selected from the group consisting of lacZY coding sequence, a firefly luciferase coding sequence, and a human growth hormone coding sequence.

17. The method of claim 2, wherein said host is an animal.

18. A selection method for the identification of one or more genes of a pathogenic microorganism, said gene(s) being specifically induced within tissue culture cells during in vivo infection of a tissue culture, comprising the steps of:

(a) isolating and fragmenting total chromosomal DNA of a first microbial strain sensitive to a first antibiotic, wherein said first strain is either (1) an auxotrophic mutant strain of said pathogenic microorganism, wherein the auxotrophic mutation is a deletion or a nonreverting mutation of a gene which is necessary for the microorganism's growth in said tissue culture cells, or (2) a strain of said pathogenic microorganism sensitive to a second antibiotic;

(b) cloning the chromosomal fragments resulting from step (a) into a suicide expression plasmid to create a library of pIVET fusion plasmids, wherein said suicide expression plasmid comprises:

(1) a gene conferring resistance to a third antibiotic, (2) a promoterless synthetic operon comprising two genes, wherein the first gene complements the auxotrophic mutation of the first microbial strain or confers resistance to the second antibiotic, and the second gene functions as a reporter gene, and (3) a cloning site 5' to the synthetic operon, wherein said cloning step fuses a chromosomal fragment to the 5' end of the promoterless synthetic operon, and wherein the chromosomal fragment provides the only region of the pIVET fusion plasmid capable of homologous recombination with the genome of the first microbial strain;

(c) amplifying the library of pIVET fusion plasmids resulting from step (b) by introducing the plasmids into a second microbial strain which provides a replication protein required for autonomous replication of said plasmids;

(d) transferring the library of pIVET fusion plasmids into cells of the first microbial strain, under conditions where the pIVET fusion plasmids may integrate by homologous recombination at the site of homology provided by the cloned chromosomal fragments and where said plasmids fall to autonomously replicate, to create a pool of fusion strains;

(e) exposing the pool of fusion strains resulting from step (d) to said third antibiotic, to select a pool of fusion strains exhibiting integration by homologous recombination;

(f) infecting said tissue culture cells with fusion strains resulting from step (e);

(g) exposing said infected tissue culture cells to said first antibiotic which is incapable of penetrating said tissue culture cells thereby killing said fusion strains which have not invaded said tissue culture cells and further treating said infected tissue culture cells with said second antibiotic if said first gene of the synthetic operon confers resistance to said second antibiotic;

(h) lysing infected tissue culture cells of step (g) and harvesting the fusion strains that survive and propagate in the tissue culture cells after step (g);

(i) plating said harvested fusion strains of step (h) on a medium that detects expression of said reporter gene; and (j) picking those fusion strains which fail to express said reporter gene in vitro, thereby identifying strains which contain a pIVET fusion plasmid integrated into a gene which is specifically induced within said tissue culture cells during in vivo infection.

19. The method of claim 18, wherein said tissue culture cells are macrophages.

20. The method of claim 18 wherein said first antibiotic is gentamicin and said second antibiotic is chloramphenicol and wherein said first promoterless gene of step (b) encodes a chloramphenicol acetyl transferase (CAT) gene.

21. A selection method for the identification of one or more genes of *Salmonella typhimurium*, said gene(s) being specifically induced during in vivo infection of a mouse, comprising the steps of:

(a) isolating and fragmenting total chromosomal DNA of a first microbial strain, wherein said first strain is a purA deficient *S. typhimurium* strain;

(b) cloning the chromosomal fragments resulting from step (a) into a suicide expression plasmid to create a library of pIVET fusion plasmids, wherein said suicide expression plasmid comprises:
 (1) a β-lactamase gene,
 (2) a mobilization fragment containing an origin of transfer,
 (3) an oriR6K origin of replication,
 (4) a promoterless synthetic operon comprising a first gene which complements the purA deficiency of the *S. typhimurium* strain, and a second lacZY coding sequence, and
 (5) a cloning site 5' to the synthetic operon, wherein said cloning step fuses a chromosomal fragment to the 5' end of the promoterless synthetic operon, and wherein the chromosomal fragment provides the only region of the pIVET fusion plasmid capable of homologous recombination with the genome of the *S. typhimurium* swain;

(c) amplifying the library of pIVET fusion plasmids resulting from step (b) by introducing the plasmids into *E. coli* comprising a pir gene encoding a Pi replication protein;

(d) transferring the library of pIVET fusion plasmids into cells of the first microbial strain, under conditions where the pIVET fusion plasmids may integrate by homologous recombination at the site of homology provided by the cloned chromosomal fragments and where said plasmids fail to autonomously replicate, to create a pool of fusion strains;

(e) exposing the pool of fusion strains resulting from step (d) to ampicillin, to select a pool of fusion strains exhibiting integration by homologous recombination;

(f) infecting said mouse with the pool of selected fusion strains resulting from step (e);

(g) harvesting from said mouse the fusion strains that survive and propagate in the mouse after step (f);

(h) plating said harvested fusion strains of step (g) on a medium that detects expression of said lacZY coding sequence; and (i) picking those fusion strains which fail to express said lacZY coding sequence in vitro, thereby identifying strains which contain a pIVET fusion plasmid integrated into a gene which is specifically induced within said mouse during in vivo infection.

* * * * *